US008232443B2

(12) United States Patent
Roeder et al.

(10) Patent No.: US 8,232,443 B2
(45) Date of Patent: Jul. 31, 2012

(54) METHOD AND DEVICE FOR INACTIVATING A MICROBIOLOGICALLY CONTAMINATED MASS CONTAINING SOLID PARTICLES WITH ACCELERATED ELECTRONS

(75) Inventors: Olaf Roeder, Dresden (DE); Henrik Flaske, Dresden (DE); Christiane Wetzel, Dresden (DE); Frank-Holm Roegner, Dresden (DE); Wolfgang Prahl, Weimar (DE); Ralf Kretzschmar, Dresden (DE); Thomas Wegner, Dresden (DE); Reinhard Boeber, Weimar (DE)

(73) Assignees: Fraunhoffer-Gesellschaft zur Foerderung der Angewandten Forschung E.V., Munich (DE); Glatt Ingenieurtechnik GmbH, Weimar (DE); Glatt Systemtechnik GmbH, Dresden (DE)

( * ) Notice: Subject to any disclaimer, the term of this patent is extended or adjusted under 35 U.S.C. 154(b) by 288 days.

(21) Appl. No.: 12/484,830

(22) Filed: Jun. 15, 2009

(65) Prior Publication Data

US 2010/0130805 A1  May 27, 2010

(30) Foreign Application Priority Data

Jun. 16, 2008  (DE) .......................... 10 2008 028 545

(51) Int. Cl.
 *A62D 3/15* (2007.01)
 *B01J 19/08* (2006.01)
(52) U.S. Cl. ......... 588/305; 250/435; 422/186; 588/405

(58) Field of Classification Search .................. 588/301, 588/305, 311, 405; 422/22, 186; 250/428, 250/431
See application file for complete search history.

(56) References Cited

U.S. PATENT DOCUMENTS

| 3,988,588 A | * | 10/1976 | Offermann ................. 250/492.3 |
| 4,230,947 A | * | 10/1980 | Cram ............................ 250/434 |
| 5,451,790 A | * | 9/1995 | Enge ............................ 250/436 |
| 2001/0042841 A1 | | 11/2001 | Lyons et al. |
| 2004/0113094 A1 | | 6/2004 | Lyons et al. |
| 2007/0248486 A1 | | 10/2007 | Morales |

FOREIGN PATENT DOCUMENTS

| DE | 199 42 142 A1 | 3/2001 |
| DE | 20 2006 015 636 | 2/2007 |
| EP | 0 024 487 | 3/1981 |
| EP | 0 931 765 | 1/1999 |
| WO | 0016615 | 3/2000 |
| WO | 02/02466 | 1/2002 |

OTHER PUBLICATIONS

E.P.O. Office action dated Sep. 12, 2011 conducted in counterpart European Patent Appln. No. 09 007 822.1.

* cited by examiner

*Primary Examiner* — Stanley Silverman
*Assistant Examiner* — Syed Iqbal
(74) *Attorney, Agent, or Firm* — Greenblum & Bernstein, P.L.C.

(57) ABSTRACT

Method and device for inactivating a microbiologically contaminated mass containing solid particles. The method includes mixing the mass containing solid particles with a gelatinizing agent, transporting the mixed mass of solid particles and gelatinizing agent through a shaping device structured so that the mixed mass, at least in one area, is shaped to form a lamellar volume with a layer thickness of between 1 mm and 3 mm, and impinging the formed lamellar volume of the mixed mass with accelerated electrons.

27 Claims, 5 Drawing Sheets

Penetration depth in μm where $\rho = 1$ g/cm$^3$ (area measurement in g/m$^2$)

Penetration depth in μm where $\rho = 1$ g/cm$^3$ (area measurement in g/m$^2$)

METHOD AND DEVICE FOR INACTIVATING A MICROBIOLOGICALLY CONTAMINATED MASS CONTAINING SOLID PARTICLES WITH ACCELERATED ELECTRONS

CROSS-REFERENCE TO RELATED APPLICATIONS

The present application claims priority under 35 U.S.C. §119 of German Patent Application No. 10 2008 028 545.5 filed Jun. 16, 2008, the disclosure of which is expressly incorporated by reference herein in its entirety.

BACKGROUND OF THE INVENTION

1. Field of the Invention

The invention relates to a method and a device for inactivating a microbiologically contaminated mass containing solid particles with accelerated electrons.

2. Discussion of Background Information

Microbiologically contaminated products or waste occur primarily in the pharmaceutical and biotechnological industry, in the course of animal testing, in the disposal of animal carcasses, in waste processing and waste water treatment and in animal production in the form of dung, to name only a few examples.

Biologically contaminated liquid or solid waste is assigned to different biosafety classes. Previously, waste of this type has been inactivated chiefly chemically or thermally, that is, the microbiological contamination in the form of viruses, bacteria, microfungi and possibly prions is eliminated.

It should be understood below under the term "inactivate" that the harmful effect to health of microbiologically contaminated constituents of a mass is eliminated. This can mean on the one hand that the microbiologically contaminated constituents of a mass are sterilized. However, on the other hand it can also already be sufficient if the adhering microorganisms are influenced such that they are no longer capable of reproduction or that the number of microorganisms capable of reproduction is reduced in order to suppress their harmful effect to health.

The type of microbiologically contaminated waste ranges from aqueous liquids to hen's eggs from vaccine production to animal carcasses such as, for example, test mice. However, dung from animal husbandry is also often contaminated with bacteria such as, e.g. salmonella, which should be inactivated before being applied to the fields.

Depending on the type of waste and contamination (dangerousness of the viruses, bacteria, microfungi or prions), known methods for inactivation are associated with risks and in part with substantial disadvantages. In particular, for example, thermal methods require considerable energy expenditure, since temperatures above 70° C. or even above 130° C. and long exposure times are necessary.

Another method is the inactivation in the course of combustion. However, in this case the product is destroyed and is not available for any further use.

Chemical methods, such as, for example, the inactivation of waste from vaccine production (e.g., hatched hen's eggs) are often based on a treatment with acids or bases. This is associated with the risk that the inactivation of larger volumes does not cover every volume element. In addition, an inline monitoring of the process and a final validation are not possible. The guarantee of biosafety can therefore be carried out only through cyclical sampling. Furthermore, this method is associated with substantial waiting times, in order to ensure the necessary minimum exposure time of the acids or bases.

A major problem with the inactivation of microbiological contaminations is often associated with the fact that the products or waste contain solids such as bones, gristle, eggshells and the like. Conventional methods are effective in these solid constituents only to a limited extent, which entails further risks in the use, the detection and in the waste disposal.

It is known that germs or microorganisms can be destroyed by accelerated electrons. For example, in DE 199 42 142 A1, bulk seeds are acted on with accelerated electrons in freefall with multiple passes through, in order to destroy germs in the bulk seeds. DE 20 2006 015 636 U1 describes pourable plant products swirled in a chamber by a gas flow that are acted on with accelerated electrons. Both of these proposals are associated with the disadvantage that they are not suitable for germ reduction in masses that have liquid constituents.

Proposals are known from the field of water treatment in which germicidal liquids are acted on with accelerated electrons (WO 02/02466 A1, EP 0 931 765 A2, EP 0 024 487 A1). Again, devices and methods of this type are not suitable for the treatment of liquids that have microbiologically contaminated solid particles, because in these proposals there are no discernible measures that prevent the sedimentation of solid particles on the base of pipes or containers. In this way, the solids precipitated there are either not acted on at all with accelerated electrons or at least not from all sides, such that the entire mass of liquid and solid constituents is not inactivated.

SUMMARY OF THE INVENTION

The invention is directed to a method and a device for inactivating a microbiologically contaminated mass containing solid particles that overcomes the disadvantages of the prior art. In particular, the method and device are suitable for the inactivation of masses containing solid particles, which can also include liquid constituents.

The solution of the technical problem results from the subject matter of the embodiments of the invention. In this regard, embodiments of the inventive method include mixing the mass containing solid particles with a gelatinizing agent, transporting the mass containing solid particles mixed with a gelatinizing agent through shaping means, in which the mass at least in one area is shaped to form a lamellar volume with a layer thickness of 1 mm to 3 mm, and acting on the mass containing solid particles and mixed with a gelatinizing agent in the lamellar volume range with accelerated electrons. Moreover, embodiments of the inventive device include a) A first device for mixing the mass containing solid particles with a gelatinizing agent, a transport device for transporting the mass containing solid particles mixed with a gelatinizing agent through shaping means, in which the mass at least in one area can be shaped to form a lamellar volume with a layer thickness of 1 mm to 3 mm, and at least one electron accelerator by which the mass containing solid particles in the lamellar volume range can be acted on with accelerated electrons.

With methods and devices according to the invention, a microbiologically contaminated mass containing solid particles is mixed with a gelatinizing agent by a suitable device. The mass containing solid particles can thereby include only solid constituents or additionally may include liquid constituents. During mixing, gelatinizing agent is to be added to the mass containing the solid particles in an amount to produce a paste-like mass, which is still pourable or pumpable, yet has a consistency that fixes the solid particles in the paste-like mass so that sedimentation of the solid particles is not possible.

It is advantageous if the mixing of the mass containing solid particles with the gelatinizing agent is carried out in a manner that the solid particles, after the mixing with the gelatinizing agent, are present in the paste-like mass in a dispersed manner. In this way, a homogenized paste-like mass is produced, i.e., the solid particles present in the paste-like mass are separately and uniformly distributed.

In embodiments, during the mixing of the mass containing solid particles and the gelatinizing agent, a liquid, such as, e.g., water is also added. This can be advantageous, for example, if the mass containing solid particles includes only solid particles or if the mass mixed with the gelatinizing agent does not yet have a pourable or pumpable consistency.

After the mass containing solid particles is mixed with a gelatinizing agent, the paste-like mass produced therefrom is transported through a shaping device. The transportation can be carried out, for example, by pumping devices, suctioning devices or pressing devices. In an area of the shaping device, the paste-like mass is shaped to form a lamellar volume with a layer thickness of 1 mm to 3 mm and this lamellar volume is acted on from at least one side with accelerated electrons, coming from at least one electron beam generator (also referred to as an electron accelerator). The area of the shaping device in which the paste-like mass can be shaped to form the lamellar volume with 1 mm to 3 mm layer thickness, is also referred to below as a slit tube.

Because the solid particles present in the paste-like mass are separately and uniformly distributed and because no deposits of solid particles on the base of the shaping device occur due to the mixed in gelatinizing agent and any liquid constituents, all of the solid particles of the paste-like mass can be acted on with accelerated electrons. Thus, microorganisms adhering to the solid particles can be inactivated. The yield, with respect to the inactivation, can be increased if the paste-like mass in the slit tube is acted on with accelerated electrons from both sides by at least two electron beam generators arranged opposite one another.

The small thickness of a slit tube of 1 mm to 3 mm produces the advantage that only electron beam generators with low acceleration voltage and radiation performance, thus, relatively cost-effective electron beam generators, are required for the complete penetration of the paste-like mass in the slit tube. Thus, the cost effectiveness of methods and devices according to the invention is increased. For example, electron accelerators with electron energy in the range of 130 keV to 800 keV are suitable for this purpose.

However, there are no restrictions at all with respect to the width of a slit tube. It needs only to be ensured that the entire width of the lamellar volume is acted on with accelerated electrons from one or more electron beam generators.

However, due to the narrow dimensions of the slit tube with respect to the slit thickness of 1 mm to 3 mm, methods and devices according to the invention are not restricted only to the inactivation of masses containing solid particles with solid particle diameters of a maximum of 1 mm. If a mass containing solid particles has solid particles with a diameter greater than 1 mm, only one additional process step, namely the breaking up of the solid particles to particles with a diameter of less than 1 mm, is necessary before the mixing with the gelatinizing agent. In the case of larger particle diameters, the breaking up can optionally also be carried out in a multiple-stage manner. Solid particles with a diameter of any size can thus also be inactivated by embodiments of the methods and devices according to the invention. In order for solid particles not to clog the slit channel, it is sufficient for the solid particles to have a diameter of 0.2 mm to 0.6 mm. However, the particles can also be reduced to still smaller dimensions.

In one embodiment the lamellar volume is acted on from both sides with accelerated electrons. The performance parameters of the electron beam generators arranged opposite one another are adjusted such that the electron energy applied to the mass containing solid particles has a maximum in the layer thickness center of the volume. Flowing volumes usually have a higher flow rate in the center of the volume than at the edges. If the performance parameters of the electron beam generators arranged opposite one another are adjusted so that the electron energy applied to the mass containing solid particles has a maximum in the layer thickness center of the volume, the energy dose applied over the slit thickness is homogenized, i.e., the constituents of the mass containing solid particles distributed over the slit thickness are then acted on with a more uniform energy dose.

In further embodiments, air, oxygen, a substance emitting oxygen, such as, e.g., a peroxide (e.g., $H_2O_2$), or another reactive gas is added during the mixing of the mass containing solid particles and the gelatinizing agent to produce a pumpable foam, which then is transported through the shaping device and acted on with accelerated electrons in the slit tube. The addition of a reactive gas or a substance emitting oxygen increases the radiosensitivity of microorganisms, whereby the necessary energy dose to be transmitted for inactivation can be reduced.

A supply of thermal energy before the impingement with accelerated electrons likewise increases the radiosensitivity of microorganisms. The heat can be produced thereby either by friction effects during the mixing and homogenization process or through additional heat-emitting physical energy sources, such as, for example, thermal radiators. Alternatively, however, the heat can also be produced through the admixture of additives that cause an exothermal chemical reaction with constituents of the mass containing solid particles and/or the gelatinizing agent.

Methyl cellulose, xanthan, locust bean gum or sodium alginate, for example, are suitable as gelatinizing agents. However, any other agent that causes a gelatinizing effect can also be used.

After the impingement with accelerated electrons, the inactivated mass is no longer harmful to human health, and, therefore, no longer needs to be subjected to a cost-intensive disposal as hazardous waste. In the now inactivated state, the mass of liquid and solid constituents can be disposed of like uncontaminated waste (such as, for example, household waste) or also supplied to reuse. The water can thus be extracted from the mass by a granulation process, for example. The granulate obtained in this manner can then be integrated into a reuse process or also easily stored over a longer period in the present form as a granulate.

Another advantage of the intermixed gelatinizing agent has an effect in the slit tube itself. The gelatinizing agent namely forms a type of lubricant film around the particles of the mass containing solid particles, which at least substantially reduces or even completely rules out the abrasion on the walls of the slit tube. It is thereby possible to embody the area of a slit tube through which electrons emitted by an electron accelerator penetrate the slit tube and strike the mass to be impinged with electrons, as a thin metal membrane in the form of an electron entry window (similar to the electron exit window of an electron beam generator) and to nevertheless ensure a high service life of the metal membrane.

Thus an electron entry window can be embodied, for example, as a metal membrane with a thickness of 8 μm to 35 μm. Thin films of titanium are particularly suitable as electron entry windows. Due to the small thickness of a metal membrane of this type, a high transparency for the electrons is achieved, which makes it possible to use electron beam generators with a relatively low acceleration voltage in a range of 150 kV to 800 kV.

In further embodiments, a metal membrane of this type can be embodied or formed as an electron entry window in the slit tube and have a supporting structure in order to absorb the pressure that forms inside the slit tube during the pumping of the mass through the slit tube. A supporting construction of this type can be embodied, for example, as a drilled plate, blades, honeycomb structure, curved wires or rods. However, when using a supporting construction, it should be ensured that no dead areas are produced for the electron beam, and that the mass in the slit tube is nevertheless acted on with electrons uniformly over the entire width of the slit tube.

The high energy of the accelerated electrons is absorbed by the slit tube and in particular by an electron entry window integrated therein in part in the form of thermal energy. It is therefore advantageous if the slit tube is suitably heat-dissipating. Thus, for example, coolant ducts, through which a coolant flows, can be integrated into the slit tube and/or into the supporting construction for an electron entry window.

In a preferred embodiment, a slit tube and an electron beam generator are embodied and aligned with respect to one another such that the electron exit window of the electron beam generator and the associated electron entry window are spaced apart from one another in the slit tube by a measurement. In the spatial area between electron exit window and electron entry window, for example, a vacuum in a range of 200 mbar to 900 mbar can be produced and monitored by a measuring device. In this manner damage to the electron exit window and to the electron entry window can be detected and a shutdown of the device be triggered. In this regard, pressure rising in the area between electron exit window and electron entry window is an indication of a defective electron entry window in the slit channel, such that the overpressure in the interior of the slit tube extends to the area between electron exit window and electron entry window. Conversely, a pressure reduction in the area between electron exit window and electron entry window is indicative of a defective electron exit window of the electron beam generator, because the vacuum of the electron beam generator evacuates the area between electron exit window and electron entry window.

Alternatively, an overpressure can also be maintained and monitored with measuring equipment in the area between the electron exit window and electron entry window.

Embodiments of the invention are directed to a method for inactivating a microbiologically contaminated mass containing solid particles. The method includes mixing the mass containing solid particles with a gelatinizing agent, transporting the mixed mass of solid particles and gelatinizing agent through a shaping device structured so that the mixed mass, at least in one area, is shaped to form a lamellar volume with a layer thickness of between 1 mm and 3 mm, and impinging the formed lamellar volume of the mixed mass with accelerated electrons.

In accordance with features of the embodiments, the method can further include breaking down the solid particles to a maximum particle size of 1 mm before the mixing. Further, the solid particles may be broken down to a particle size within a range of 0.2 mm to 0.6 mm.

According to further features of the embodiments, the method can include mixing the mass containing solid particles with a liquid.

Further, the transporting of the mixed mass may include at least one of pumping, suctioning, and pressing the mixed mass through the shaping device.

In accordance with other features of the embodiments, the formed lamellar volume of the mixed mass can be impinged on one side by accelerated electrons from an electron beam generator. Alternatively, the formed lamellar volume of the mixed mass can be impinged on two sides by accelerated electrons from at least two electron beam generators arranged opposite one another. The method can also include adjusting performance parameters of the at least two electron beam generators so that a maximum electron energy is applied to a center of layer thickness of the formed lamellar volume of the mixed mass.

According to other features of the embodiments of the invention, the method can also include foaming the mass containing solid particles with a gas before the impinging of the formed lamellar volume of the mixed mass with accelerated electrons.

The method may further include heating the mass containing solid particles with a heater before the impinging of the formed lamellar volume of the mixed mass with accelerated electrons. Further, the heater can include additives causing an exothermal chemical reaction with constituents of the mass containing solid particles. Still further, the heater may include a physical energy source.

The method can also include extracting liquid from the mixed mass after impinging the mixed mass with accelerated electrons.

Embodiments of the invention are directed to a device for inactivating a microbiologically contaminated mass containing solid particles. The device includes a mixer arranged to mix the mass containing solid particles with a gelatinizing agent, a transporter arranged to transporting the mixed mass of solid particles and gelatinizing agent through a shaper structured to form a lamellar volume with a layer thickness between 1 mm and 3 mm, and at least one electron accelerator arranged to impinge the formed lamellar volume mixed mass with accelerated electrons.

According to features of the embodiments of the present invention, the at least one electron accelerator can include at least two electron accelerators positionable opposite one another to impinge two sides of the formed lamellar volume mixed mass with accelerated electrons.

In accordance with other features of the embodiments, at least one electron entry window can be formed in an area of the shaper to pass the accelerated electrons from the at least one electron accelerator to the formed lamellar volume mixed mass. The at least one electron entry window can include a metal membrane with a thickness between 8 μm and 35 μm. Further, the at least one electron entry window may include a supporting device.

According to further features, an electron energy of the at least one electron accelerator can be within a range of 130 keV to 800 keV.

Moreover, the at least one electron accelerator may include an electron exit window arranged to form a spaced area from a respective at least one electron entry window of the shaper. The spaced area between the electron exit window and the electron entry window can be filled with a protective gas. Further, the spaced area between the electron exit window and the electron entry window may be under vacuum. Still further, the spaced area between the electron exit window and the electron entry window can be under an overpressure. Further, a measuring device can be arranged to detect a pressure change in the spaced area between the electron exit window and the electron entry window.

In accordance with still yet other features of the embodiments of the present invention, the transporter can include a device for at least one of pumping, suctioning, and pressing.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
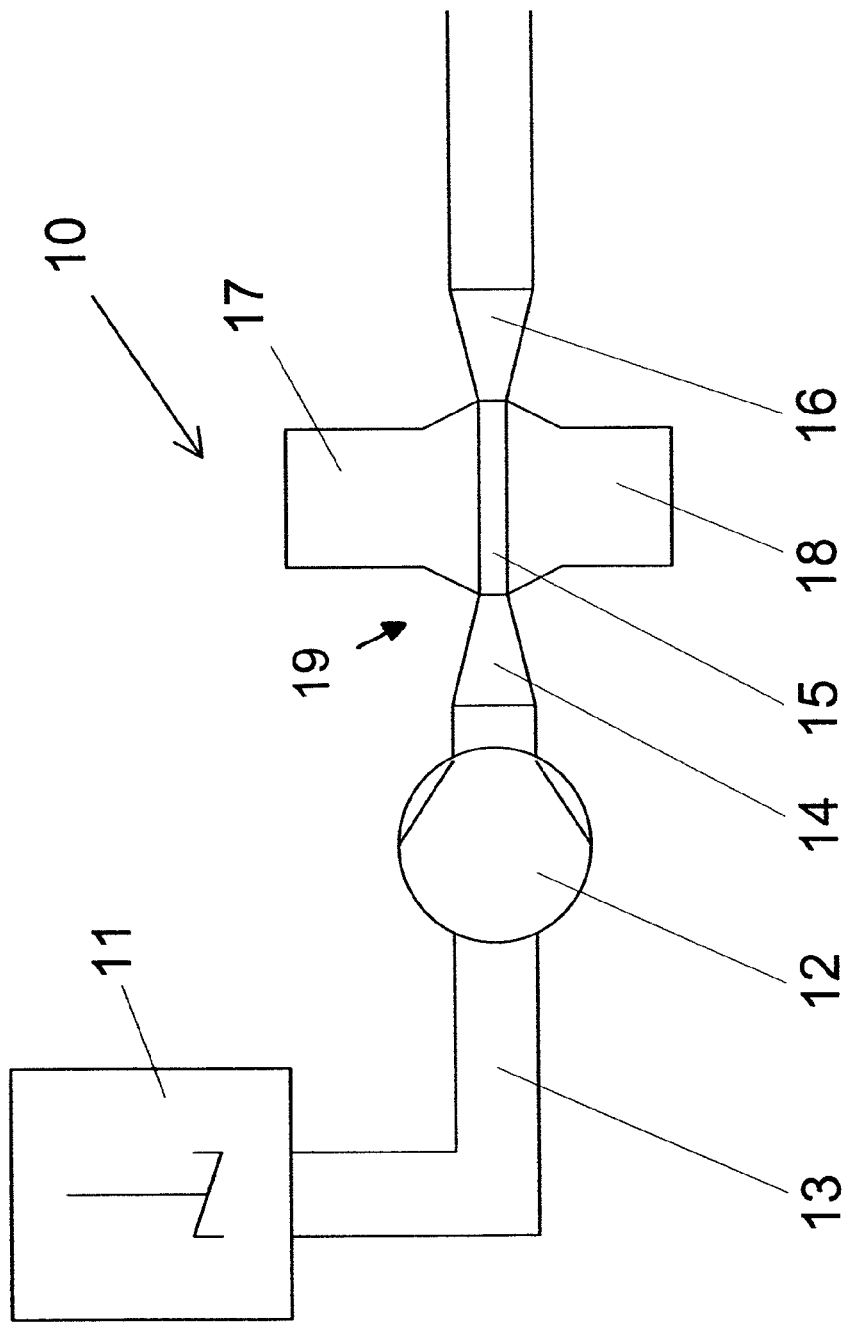
FIG. 1 diagrammatically represents an embodiment of a device according to the invention for inactivating waste.

FIG. 1 illustrates an embodiment of a device according to the invention for inactivating waste, e.g., from the pharmaceutical industry. By way of non-limiting example, in the production of sera for anti-influenza inoculations, hen's eggs are infected with influenza virus. After some time of incubation and after the viruses in the eggs have multiplied by a multiple, a liquid is now "harvested," i.e., extracted from the eggs and in further processing steps sera are obtained therefrom for inoculation. Egg residue is left behind, comprising eggshells, embryos and possibly also egg white and egg yolk, which are respectively contaminated with influenza viruses.

This egg residue is to be inactivated with a device 10 according to the invention shown diagrammatically in FIG. 1, i.e., it is at least to be ensured that the influenza viruses adhering to the egg residue are no longer capable of reproduction. In this way, the egg residue no longer poses any risk to human health.

In a first step, the solid particles of the mass comprising solid and liquid egg residue is broken up using a device (not graphically shown) in several stages to an ultimate particle size of no more than 0.5 mm and this solid and liquid egg residue is then subsequently mixed in a container 11 with methyl cellulose acting as a gelatinizing agent.

The mixing is carried out in such a manner that the solid particles are dispersed in the produced or resulting paste-like mass contaminated with viruses, and the paste-like mass has a consistency that holds the solid particles in a "floating" manner, i.e., no sedimentation of the solid particles occurs. During the mixing, the contaminated mass is at the same time foamed with 10% by volume air and heated to a temperature of 50° C.

The now homogenized paste-like mass is transported by a pump 12 initially through pipelines 13 and subsequently through a shaping device 19. Shaping device 19 comprises a transition piece 14, in which a circular pipe cross section is transformed into a rectangular cross section, a slit tube 15, in which the rectangular cross section is maintained and the contaminated mass thus takes on a constant lamellar volume having, e.g., a 2 mm layer thickness and a 100 mm width, and a transition piece 16, in which the rectangular pipe cross section is transformed back again to a round cross section. The renewed change of the cross section after passing through slit tube 15 is not essential to the invention, but in the concrete exemplary embodiment simplifies the pipe guidance following slit tube 15.

In the area of the slit tube 15, the lamellar mass is acted on with accelerated electrons from at least one and preferably both sides by electron beam accelerators 17 and/or 18, which are arranged opposite one another. In this way, the lamellar mass is inactivated, i.e., the influenza viruses either present in the paste-like mass or adhering to the solid particles are killed or are at least no longer capable of reproduction after the impingement with accelerated electrons, thus no longer posing a risk to human health.

The two electron beam generators 17 and 18 respectively comprise a so-called axial emitter and an associated beam deflection with deflection control, by which the electron beam generated by the axial emitter is deflected. Both of the electron beam generators 17 and 18 therefore act as area beam generators.

After the mass has passed through shaping device 19 and has been impinged with accelerated electrons, the water is extracted from the now inactivated mass in a granulation process with suitable devices (not shown). As a result, a high-quality granulate is produced hereby, which comprises primarily egg white, and which can be fed to a reuse, such as, e.g., animal feed or as an additive in the production of fertilizer.

Figure 2:
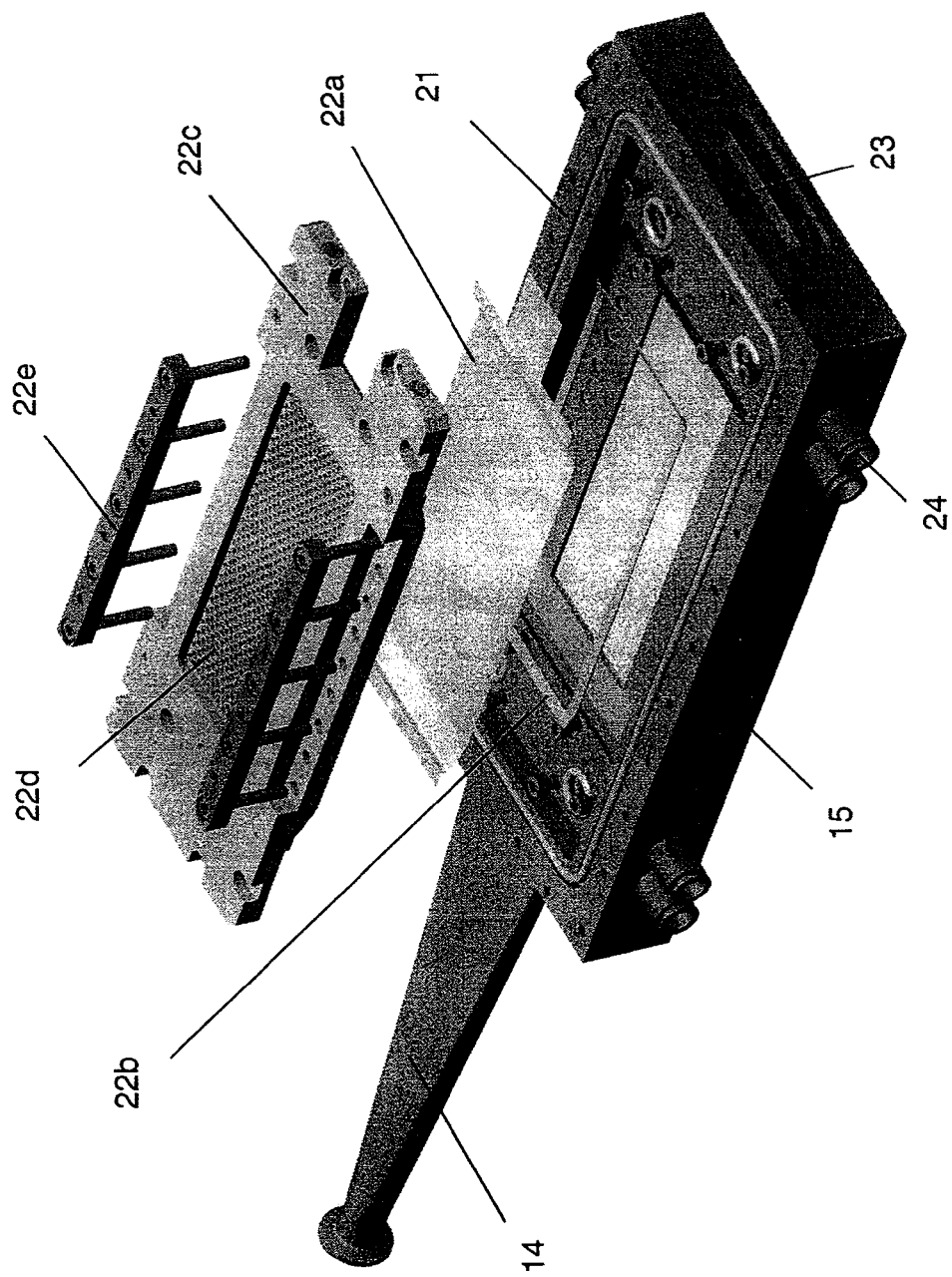
FIG. 2 illustrates in greater detail the slit tube depicted in FIG. 1 with a perspective exploded view of an upper electron entry window.

In FIG. 2, slit tube 15 from FIG. 1, as well as entry-side transition piece 14, is diagrammatically illustrated in a perspective and part exploded view. Slit tube 15 comprises a base body 21, an upper electron entry window 22, and a corresponding lower electron entry window (not shown in FIG. 2) that is embodied or formed like electron entry window 22. On the exit side of slit tube 15 is an end of a slit 23 that runs through slit tube 15 so as to guide the contaminated mass as it is pumped through slit tube 15.

Electron entry window 22 comprises a titanium film 22a, a sealing element 22b, a supporting construction 22c with a perforated area 22d, and mounting elements 22e. Titanium film 22a can be 25 μm thick and, in the assembled state, can form a part of the interior wall of slit tube 15 that is in direct contact with the mass pumped through slit tube 15, while sealing element 22b can be arranged between base body 21 and titanium film 22a. Supporting construction 22c includes a perforated area 22d, through which the electron beam generated by electron beam generator 17 is deflected, and mounting elements 22e are provided to attach electron entry window 22 to base body 21. With supporting construction 22c attached to base body 21, the pressure from the interior of slit tube 15, which is produced when the contaminated mass is pumped through slit tube 15, is absorbed. In this way, embodiments of the invention avoid undesired bulges or increases in the thickness of slit 23 that may result from thin titanium film 22a alone not being able to withstand this interior pressure of slit tube 15. These bulges or thickness increases of slit 23 could also lead to a more inhomogeneous radiation result of the contaminated mass, seen via the layer thickness of the volume Several connections 24 for coolant lines are likewise visible in FIG. 2. Several channels (not shown) can run through base body 21 in order to guide coolant from the coolant lines, such that the thermal energy produced during the passage of the accelerated electrons through the two electron entry windows and expanding throughout the entire slit tube 15 due to heat conduction, can be dissipated.

Figure 3:
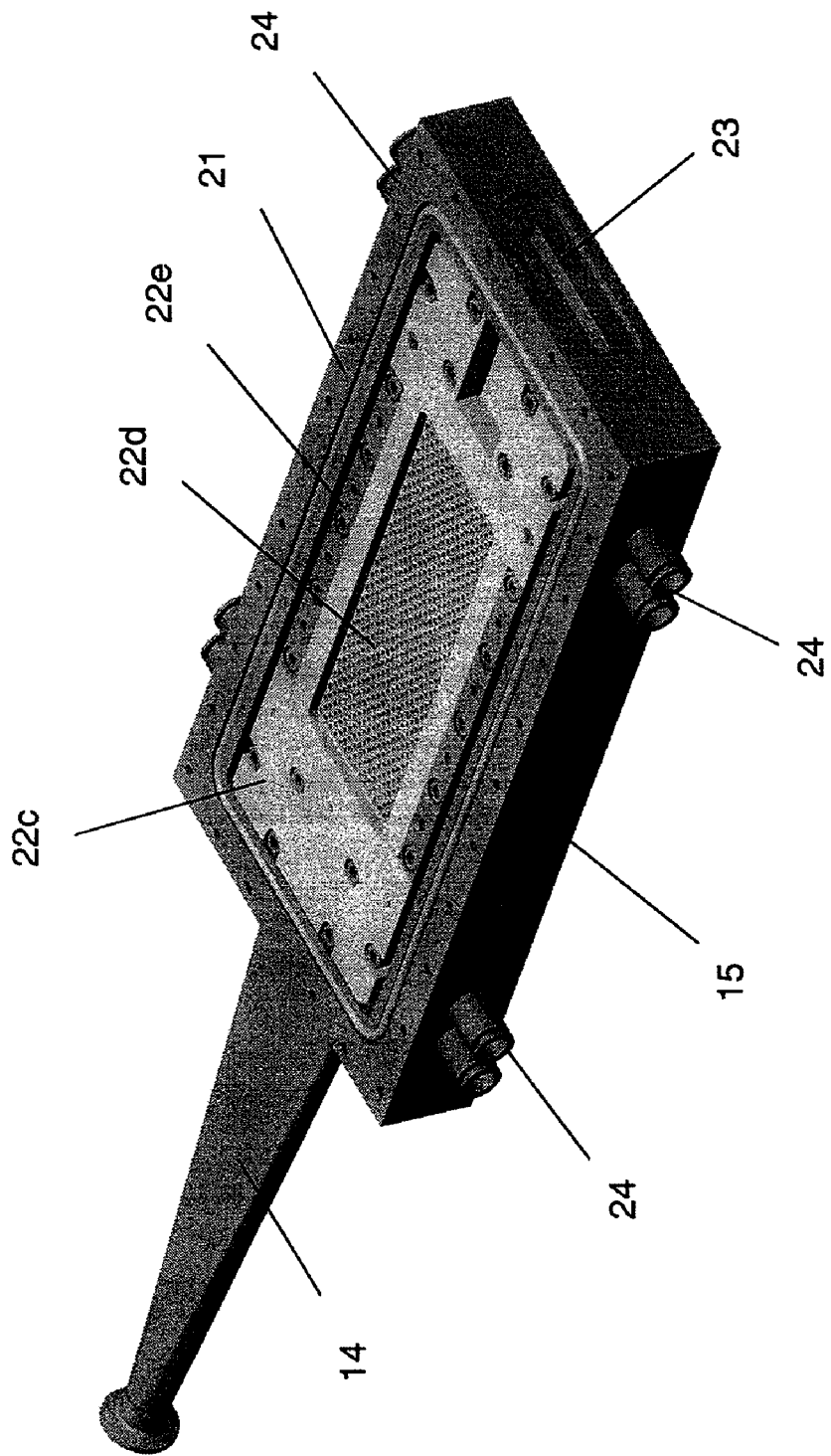
FIG. 3 illustrates in greater detail the slit tube depicted in FIG. 1 in an assembled state.

FIG. 3 diagrammatically shows slit tube 15 with transition piece 14 on the entry side in a perspective representation. However, in contrast to the depiction in FIG. 2, FIG. 3 shows the slit tube 15 in the assembled state, such that not all of the components shown in FIG. 2 are discernible in FIG. 3.

Figure 4:
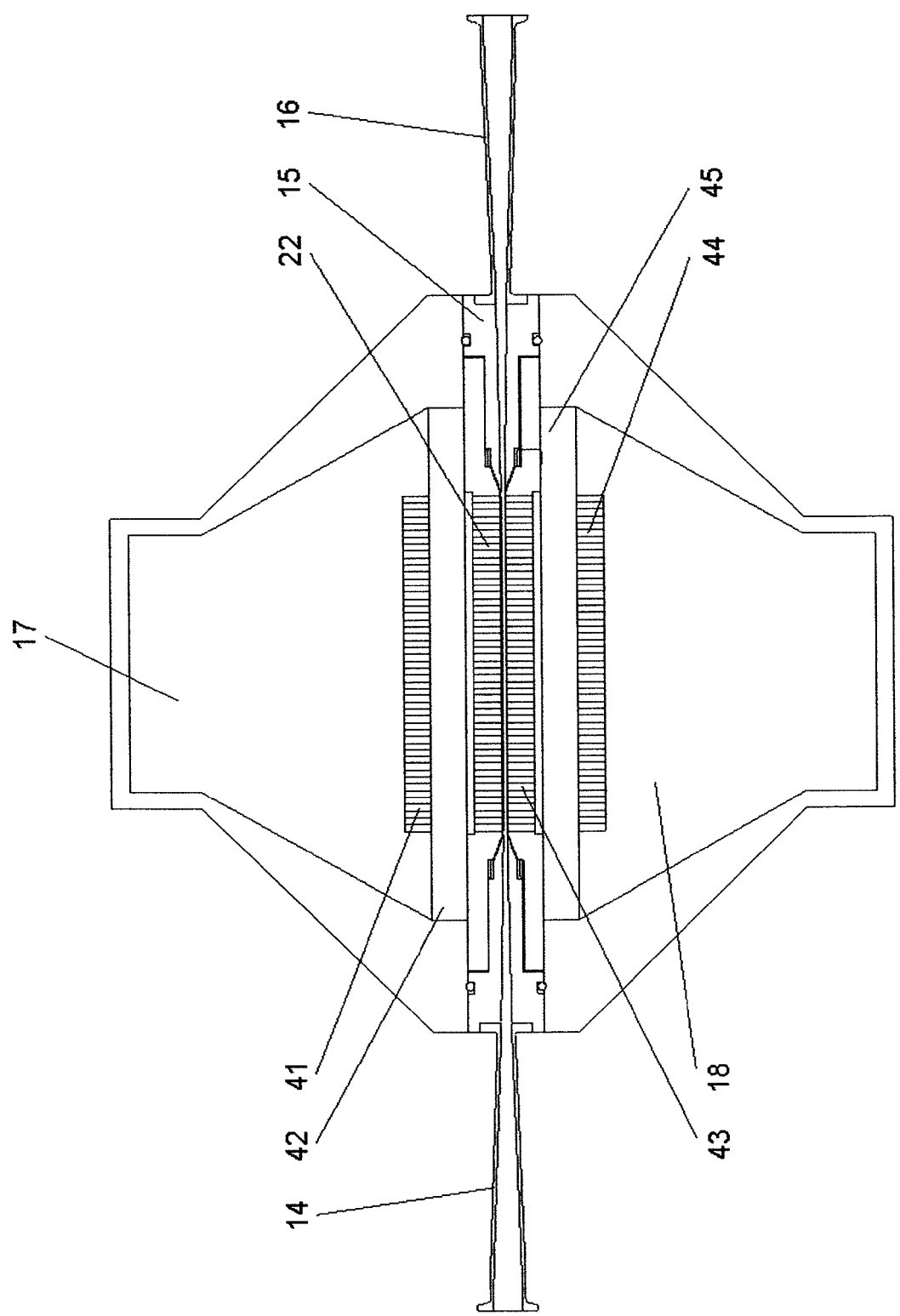
FIG. 4 diagrammatically illustrates a cross-section of the slit tube with upper and lower electron beam generators depicted in FIG. 1.

A diagrammatic cross-sectional representation of slit tube 15 with transition pieces 14 and 16 and flange-mounted electron beam generators 17 and 18 is shown in FIG. 4. Electron beam generator 17, which comprises an electron exit window 41, is attached to the slit tube 15. Electron beam generator 17 is thereby positioned so that its flat electron exit window 41 is arranged parallel to and opposite the likewise flat electron entry window 22. For the sake of completeness, it should be mentioned once again that the electron window 22 comprises the partial elements 22a, 22b, 22c, 22d and 22e shown in FIG. 2. Moreover, both windows 41 and 22 are spaced apart from one another by a measurement of, e.g., 30 mm to delimit an area 42 that is filled with a protective gas, such as nitrogen, to an absolute value of 800 mbar. This vacuum is maintained with suitable devices (not shown).

The electrons produced and accelerated by the electron beam generator 17 therefore pass through electron exit window 41, span area 42, subsequently pass through electron entry window 22 in order to act on the contaminated mass that is being pumped through slit tube 15.

The pressure conditions in area 42 are monitored with a measuring device (not shown). When a first pressure threshold value is exceeded, just as in the case of falling below a smaller second pressure threshold value, a warning signal is triggered and/or the entire installation is switched off. Such action is taken because exceeding the first pressure threshold value is an indication of a leaking or defective electron entry window 22 and falling below the second threshold value is an indication of a leaking or defective electron exit window 41.

Electron beam generator 18 is flange-mounted on the lower electron entry window 43 of the slit tube 15 in a mirror symmetrical manner to the electron beam generator 17 and with the same structure and the same mode of operation. Here too electron exit windows 44 of the electron beam generator 18 and the associated electron entry window 43 of slit tube 15 are spaced apart by a measurement of, e.g., 30 mm to delimit an area 45 that is filled with a protective gas, such as nitrogen, under vacuum conditions such as 800 mbar, monitored by a suitable measuring device.

The guiding of the contaminated mass through slit tube 15 is carried out continuously between the two electron entry windows 22 and 43, whereby the entire volume of the mass flowing through is acted on with electron energy. The highest flow rate naturally prevails in the center of the flow cross section of channel 23 as compared to the interface at the channel wall or electron entry window, such that with homogeneous energy input, the lowest energy dose would be transferred in the center of the slit. This minimum is compensated through the choice of an optimal acceleration voltage for both electron accelerators 17 and 18.

Figure 5A:
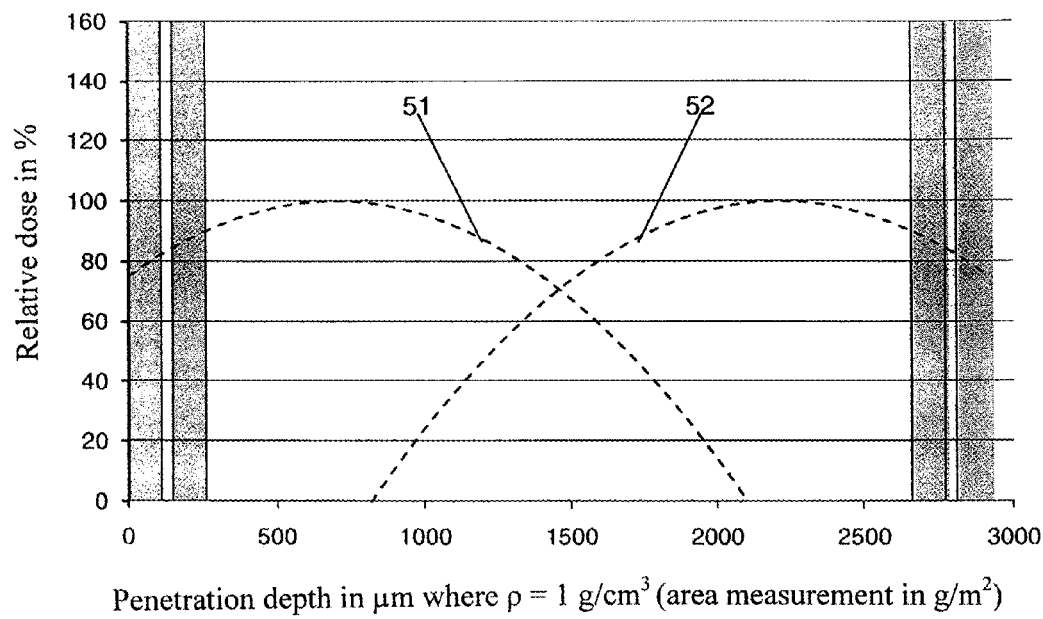
FIGS. 5a and 5b illustrate relative dose distributions of the electrons accelerated by electron beam generators 17 and 18.

FIG. 5a shows graphically the exemplary relative depth dose distribution of an arrangement according to embodiments of the invention for the two electron accelerators 17 and 18 depicted in FIG. 4, in which a thickness of the titanium films of electron exit windows 41 and 44 is 25 μm with an acceleration voltage of 500 kV, a distance between electron exit windows 41 and 44 and respectively associated electron entry windows 22 and 43 is 30 mm, a thickness of the titanium films of electron entry windows 22 and 43 is 25 μm, and a layer thickness of the contaminated mass in channel 23 of slit tube 15 is 2 mm.

The dashed curve 51 represents the distribution of the energy dose generated by electron accelerator 17, over the penetration depth of the electrons accelerated. The zero point of the horizontal axis corresponds to the position at which the accelerated electrons of electron beam generator 17 strike the titanium film of its electron exit window 41. The first dark bar 53 on the left therefore represents the titanium film of the electron exit window 41, and the second dark bar 54 on the left represents the titanium film of the electron entry window 22.

Upon exiting from the titanium film of electron exit window 41, an energy dose of approx. 80% is achieved. With increasing penetration depth, this dose increases further until it reaches its maximum at about 700 μm (here the electrons are already located inside the mass to be acted on in the slit tube 15). With further increasing penetration depth, the energy dose now decreases, until the energy of the electrons has dropped to a value of zero at a penetration depth that corresponds to approx. 2,100 μm at a density of 1 g/cm$^3$. The accelerated electrons of the electron beam generator 17 thus do not reach the electron entry window 43 lying opposite, but already emit their energy fully even before the contaminated mass has been completely penetrated in its layer thickness. From the other side, however, the contaminated mass is acted on with the accelerated electrons by the electron beam generator 18.

The two dark bars 55 and 56 on the right side correspond in a mirror symmetrical manner to the two titanium films of electron exit window 44 and electron entry window 43 depicted by dark bars 54 and 53, respectively. The distribution of the energy dose produced by electron accelerator 18 over the penetration depth of the electrons accelerated thereby is shown with the dashed curve 52.

Figure 5B:
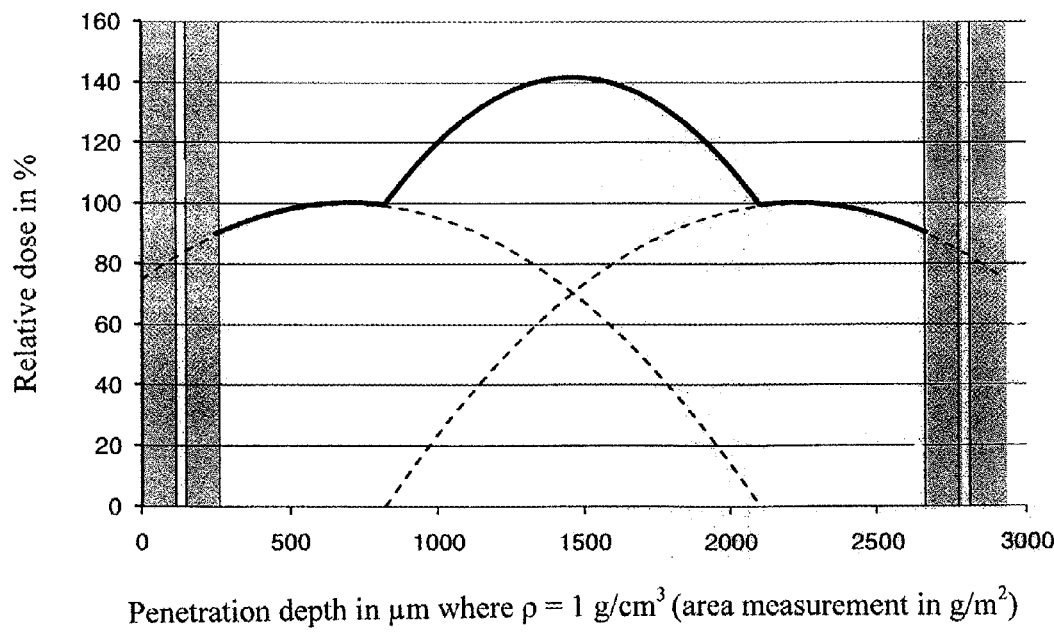

It is discernible that a central area with respect to the layer thickness of the mass to be irradiated is acted on from both sides with accelerated electrons. The energy dose is thus also increased in this area. The curve from the sum of the energy dose supplied from both sides is shown as a continuous curve in FIG. 5b. This shows a maximum in the center of the slit tube. Through this rise in the dose the increased flow rate in the slit tube center is compensated and a largely homogenous energy dose results over the entire volume of the mass flowing through the slit tube.

Although the exemplary embodiment is concretely described with respect to the inactivation of hatching egg waste from the pharmaceutical industry, methods and devices according to the invention are also suitable, however, for inactivating all microbiologically contaminated masses, the solid constituents of which can be broken down to a maximum particle size of 1 mm.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for inactivating a microbiologically contaminated mass containing solid particles, comprising:
   mixing the mass containing solid particles with a gelatinizing agent;
   transporting the mixed mass of solid particles and gelatinizing agent through a shaping device structured so that the mixed mass, at least in one area, is shaped to form a lamellar volume with a layer thickness of between 1 mm and 3 mm; and
   impinging the formed lamellar volume of the mixed mass with accelerated electrons.

2. The method in accordance with claim 1, further comprising breaking down the solid particles to a maximum particle size of 1 mm before the mixing.

3. The method in accordance with claim 2, wherein the solid particles are broken down to a particle size within a range of 0.2 mm to 0.6 mm.

4. The method in accordance with claim 1, further comprising mixing the mass containing solid particles with a liquid.

5. The method in accordance with claim 1, wherein the transporting of the mixed mass comprises at least one of pumping, suctioning, or pressing the mixed mass through the shaping device.

6. The method in accordance with claim 1, wherein the formed lamellar volume of the mixed mass is impinged on one side by accelerated electrons from an electron beam generator.

7. The method in accordance with claim 1, wherein the formed lamellar volume of the mixed mass is impinged on two sides by accelerated electrons from at least two electron beam generators arranged opposite one another.

8. The method in accordance with claim 7, further comprising adjusting performance parameters of the at least two electron beam generators so that a maximum electron energy is applied to a center of layer thickness of the formed lamellar volume of the mixed mass.

9. The method in accordance with claim 1, further comprising foaming the mass containing solid particles with a gas before the impinging of the formed lamellar volume of the mixed mass with accelerated electrons.

10. The method in accordance with claim 1, further comprising heating the mass containing solid particles with a heater before the impinging of the formed lamellar volume of the mixed mass with accelerated electrons.

11. The method in accordance with claim 10, wherein the heater comprises additives causing an exothermal chemical reaction with constituents of the mass containing solid particles.

12. The method in accordance with claim 10, wherein the heater comprises a physical energy source.

13. The method in accordance with claim 1, further comprising extracting liquid from the mixed mass after impinging the mixed mass with accelerated electrons.

14. The method in accordance with claim 1, wherein the mixing disperses the solid particles in the mixed mass.

15. A device for inactivating a microbiologically contaminated mass containing solid particles, comprising:
   a mixer arranged to mix the mass containing solid particles with a gelatinizing agent;
   a transporter arranged to transporting the mixed mass of solid particles and gelatinizing agent through a shaper structured to form a lamellar volume with a layer thickness between 1 mm and 3 mm; and
   at least one electron accelerator arranged to impinge the formed lamellar volume mixed mass with accelerated electrons.

16. The device in accordance with claim 15, wherein the at least one electron accelerator comprises at least two electron accelerators positionable opposite one another to impinge two sides of the formed lamellar volume mixed mass with accelerated electrons.

17. The device in accordance with claim 15, further comprising at least one electron entry window formed in an area of the shaper to pass the accelerated electrons from the at least one electron accelerator to the formed lamellar volume mixed mass.

18. The device in accordance with claim 17, wherein the at least one electron entry window comprises a metal membrane with a thickness between 8 μm and 35 μm.

19. The device in accordance with claim 17, wherein the at least one electron entry window comprises a supporting device.

20. The device in accordance with claim 15, wherein an electron energy of the at least one electron accelerator is within a range of 130 keV to 800 keV.

21. The device in accordance with claim 15, wherein the at least one electron accelerator comprises an electron exit window arranged to form a spaced area from a respective at least one electron entry window of the shaper.

22. The device in accordance with claim 21, wherein the spaced area between the electron exit window and the electron entry window is filled with a protective gas.

23. The device in accordance with claim 21, wherein the spaced area between the electron exit window and the electron entry window is under vacuum.

24. The device in accordance with claim 21, wherein the spaced area between the electron exit window and the electron entry window is under an overpressure.

25. The device in accordance with claim 21, further comprising a measuring device arranged to detect a pressure change in the spaced area between the electron exit window and the electron entry window.

26. The device in accordance with claim 15, wherein the transporter comprises a device for at least one of pumping, suctioning, or pressing.

27. The device in accordance with claim 15, wherein the mixer is structured to disperse the solid particles in the mixed mass.

* * * * *